US009516860B2

(12) United States Patent
Toth

(10) Patent No.: US 9,516,860 B2
(45) Date of Patent: Dec. 13, 2016

(54) ANIMAL MONITORING SYSTEM AND METHOD

(71) Applicant: Thrive Solutions Ltd., Regina (CA)

(72) Inventor: Joseph Mervin Toth, Regina (CA)

(73) Assignee: THRIVE SOLUTIONS LTD., Regina, Saskatchewan (CA)

( * ) Notice: Subject to any disclaimer, the term of this patent is extended or adjusted under 35 U.S.C. 154(b) by 168 days.

(21) Appl. No.: 14/455,221

(22) Filed: Aug. 8, 2014

(65) Prior Publication Data

US 2015/0097668 A1   Apr. 9, 2015

Related U.S. Application Data

(60) Provisional application No. 61/886,968, filed on Oct. 4, 2013.

(51) Int. Cl.
| | |
|---|---|
| G08B 1/08 | (2006.01) |
| A01K 11/00 | (2006.01) |
| A01K 15/02 | (2006.01) |
| A61B 5/024 | (2006.01) |
| A61B 5/01 | (2006.01) |
| A61B 5/00 | (2006.01) |
| G08B 21/02 | (2006.01) |

(52) U.S. Cl.
CPC .......... *A01K 11/008* (2013.01); *A01K 15/023* (2013.01); *A61B 5/02438* (2013.01); *G08B 21/0261* (2013.01); *A61B 5/0022* (2013.01); *A61B 5/01* (2013.01); *A61B 2503/40* (2013.01); *G08B 21/023* (2013.01); *G08B 21/0211* (2013.01); *G08B 21/0272* (2013.01)

(58) Field of Classification Search
CPC ..... A01K 11/008; A01K 15/023; A61B 5/002; A61B 5/01; A61B 5/02438
See application file for complete search history.

(56) References Cited

U.S. PATENT DOCUMENTS

| | | | | |
|---|---|---|---|---|
| 5,791,294 | A | † | 8/1998 | Manning |
| 5,868,100 | A | † | 2/1999 | Marsh |
| 5,963,130 | A | * | 10/1999 | Schlager ............ G08B 21/0453 340/501 |
| 6,043,748 | A | † | 3/2000 | Touchton |
| 6,232,880 | B1 | † | 5/2001 | Anderson |

(Continued)

*Primary Examiner* — Omeed Alizada
(74) *Attorney, Agent, or Firm* — Ryan W. Dupuis; Kyle R. Satterthwaite; Ade & Company Inc

(57) ABSTRACT

An animal monitoring system has sensor modules carried on respective animals. Each module includes a GPS position locator to determine a current position of the animal, a transmitter, and a controller arranged to store a previously determined position of the animal thereon. A central monitoring system is located remotely from the animal which stores boundary position data representing a boundary thereon and which is arranged to communicate with the sensor module over a network. If the position of the animal changes significantly, a notification signal is transmitted to the central monitoring system which compares the current position to the boundary position data to determine is a user should be notified of an alarm condition. The sensor modules may also monitor various physiological characteristics of the animal to notify the central monitor system and subsequently the user if the animal appears to be in danger.

20 Claims, 1 Drawing Sheet

(56) References Cited

U.S. PATENT DOCUMENTS

| | | | |
|---|---|---|---|
| 6,232,916 B1 † | 5/2001 | Grillo | |
| 6,271,757 B1 † | 8/2001 | Touchton | |
| 6,487,992 B1 † | 12/2002 | Hollis | |
| 6,581,546 B1 † | 6/2003 | Dalland | |
| 6,700,492 B2 † | 3/2004 | Touchton | |
| 6,903,682 B1 † | 6/2005 | Maddox | |
| 8,188,869 B2 | 5/2012 | Wangrud | |
| 2005/0062604 A1* | 3/2005 | Fong | G08B 21/0236 340/539.23 |
| 2009/0048498 A1* | 2/2009 | Riskey | A61B 5/0031 600/302 |
| 2012/0161958 A1* | 6/2012 | Turon | G01S 19/34 340/539.3 |
| 2013/0127658 A1 † | 5/2013 | McFarland | |

\* cited by examiner
† cited by third party

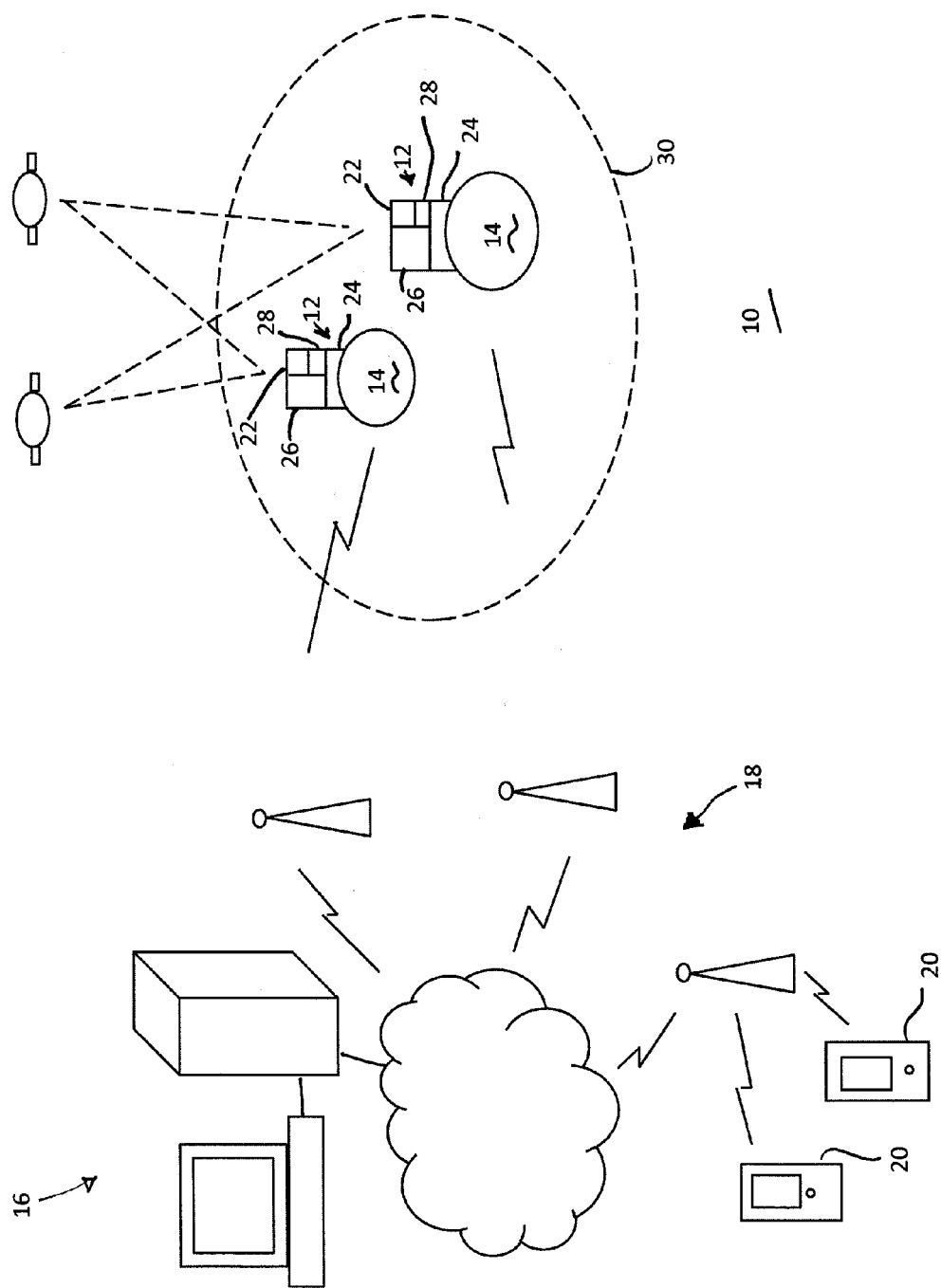

ANIMAL MONITORING SYSTEM AND METHOD

This application claims the benefit under 35 U.S.C. 119(e) of U.S. provisional application Ser. No. 61/886,968, filed Oct. 4, 2013.

FIELD OF THE INVENTION

The present invention relates to an animal monitoring system for monitoring a condition, for example location, heart rate, etc., of animals, including livestock or other animal populations, and more particularly the present invention relates to method of using the monitoring system to transmit notifications over a communication network indicative of an alarm condition relating to the animal, for example theft of the animal, poor health of the animal, or proximity of an animal to vehicular traffic.

BACKGROUND

In the field of animal husbandry the loss of animals due to illness, loss to predators, or theft can be costly to the owners of the animals. Accordingly it is known to be desirable to employ monitoring systems to track the location of animals, particularly livestock animals, to attempt to minimize losses.

U.S. Pat. No. 8,188,869 by Wangrud discloses one example of a kit and method for monitoring and tracking animals using a GPS locator implanted subcutaneously into an animal for transmission to a smartphone. The smartphone then determines if the animal is outside of a respective boundary which indicates a potential theft of an animal or an animal which has broken free of its enclosure. The locator implanted on the animal must regularly transmit its position to the smarthphone to determine if an alarm condition exists, however, the continuous transmission of data requires considerable battery power and available bandwidth for large herds.

SUMMARY OF THE INVENTION

According to one aspect of the invention there is provided a method of monitoring an animal comprising:
  i) providing a monitoring system including:
    a sensor module arranged to be carried on the animal which includes a position locator arranged to receive position data from a satellite network and determine a current position of the animal, a transmitter, and a controller arranged to store a previously determined position of the animal thereon; and
    a central monitoring system located remotely from the animal which stores boundary position data representing a boundary thereon and which is arranged to communicate with the sensor module over a network;
  ii) periodically sensing a position of the animal using the position locator of the sensor module;
  iii) comparing the current position to a previously determined position to determine a notification condition if the position of the animal has substantially changed using the controller of the sensor module;
  iv) transmitting a notification signal which includes the current position to the central monitoring system over a network using the transmitter of the sensor module in response to determination of the notification condition; and
  v) comparing the current position to the boundary position data using the central monitoring system to determine an alarm condition if the current position is outside of the boundary represented by the boundary position data.

By only transmitting the position of the animal when the position changes, there is no need for transmission of the data when the animal is at rest. Accordingly battery consumption and bandwidth requirements are considerably reduced.

Preferably an alert is sent from the central monitoring system to an owner of the animal if an alarm condition has been determined. Preferably the alert includes the current position of the animal.

The method may include increasing a frequency of the periodic sensing of the position of the animal if an alarm condition has been determined.

Preferably the frequency of the periodic sensing of the position of the animal is also increased if a rate of change of the position of the animal exceeds a prescribed speed limit, which may indicate theft of the animal being carried on a transport vehicle for example.

Preferably the notification signal is transmitted from the sensor module to the central monitoring system over of a mobile communication network.

The alert may be sent from the central monitoring system to a plurality of subscribers if an alarm condition has been determined. This is particularly suited to a plurality of mobile phone users having an application executable on their phone which communicates with the central monitoring system so as to be arranged to receive alerts on the mobile phone over the mobile phone network. When the boundary is defined alongside a roadway, the animal may comprise any kind of wild animal or domesticated livestock animal, for example cattle, horses, pigs, sheep, goats, bison, elk, lammas, donkeys, dogs, cats, etc.

In this instance a subscriber having the executable application on their mobile phone will receive an alert that the animal is near the roadway. The application on the mobile phone of the user preferable also considers the location of the user in their vehicle so that the defined boundary is in sufficient proximity to the user that there is a potential for a collision between the wild animal and the user.

More preferably, the animal comprises a livestock animal. The system in this instance may include both a position locator and a condition sensor on the sensor module such that the condition sensor is arranged to sense a condition of the animal. The method may then further include: i) storing a prescribed condition criterion on the controller of the sensor module, and ii) transmitting a notification signal which includes the sensed condition of the animal to the central monitoring system if the sensed condition of the animal meets the prescribed condition criterion.

According to a second aspect of the present invention there is provided a method of monitoring an animal comprising:
  i) providing a monitoring system including:
    a sensor module arranged to be carried on the animal which includes a condition sensor on the sensor module which is arranged to sense a condition of the animal, a transmitter, and a controller arranged to store a prescribed condition criterion of the animal thereon; and
    a central monitoring system located remotely from the animal which stores boundary position data representing a boundary thereon and which is arranged to communicate with the sensor module over a network;
  ii) periodically sensing a condition of the animal using the condition sensor of the sensor module;

iii) comparing the sensed condition to the prescribed condition criterion to determine a notification condition using the controller of the sensor module; and iv) transmitting a notification signal which includes the sensed condition of the animal to the central monitoring system if the sensed condition of the animal meets the prescribed condition criterion.

The notification signal may further include the current position of the animal.

The condition of the animal may be a heart rate of the animal or a body temperature of the animal for example.

An alarm condition may be determined by the central monitoring system by comparing the sensed condition to a previously sensed condition of the animal and an ambient condition, for example temperature.

The method may further include increasing a frequency of the periodic sensing of the position of the animal if an alarm condition is determined.

Some embodiments of the invention will now be described in conjunction with the accompanying drawings in which:

BRIEF DESCRIPTION OF THE DRAWINGS

FIG. 1 is a schematic representation of the animal monitoring system.

In the drawings like characters of reference indicate corresponding parts in the different FIGURES.

DETAILED DESCRIPTION

Referring to the accompanying FIGURES there is illustrated a system for monitoring one or more animals of an animal population as generally indicated by reference numeral 10. The system 10 is particularly suited for monitoring location and condition of livestock or for monitoring proximity of wild animals to roadways and the like.

The system 10 generally includes a plurality of sensor modules 12 arranged to be supported on respective ones of the animals 14. The sensor modules 12 communicate with a central monitoring system 16 through a network 18, for example a terrestrial cellular network, a satellite modem network such as iridium or other satellite modems for two way data transmission from/to the animal and the central monitoring system. The central monitoring system 16 is then arranged to in turn communicate with a plurality of mobile devices 20 belonging to users of the system also through the cellular network.

Each sensor module 12 generally comprises a single housing arranged to be carried on the animal using suitable adhesive for attachment externally on the skin at a location between the shoulder blades of the animal. Alternatively the housing may be suitably arranged for injection subcutaneously under the skin of the animal. In a further instance, the housing may be attached by piercing into any part of the body such as into the ear or chest.

The single housing of each module 12 includes a position locator 22 and one or more condition sensors 24 powered by a respective battery also received within the housing. The battery also powers a transceiver 26 and a controller 28 also carried within the housing. The housing may also include a component arranged to automatically read RFID ear tags to automatically obtain an animal identifier to be included in all transmissions relating to the module.

The position locator 22 comprises a suitable device arranged to communicate with a global positioning satellite network to communicate position data therebetween to identify the longitudinal and latitudinal position of the module and the animal upon which it is supported.

The condition sensors 24 may take various forms for sensing various conditions of the animal and of the ambient conditions. Conditions of the animal include the heart rate of the animal, the internal body temperature of the animal, or any other conditions which may be indicative of the health of the animal. The ambient conditions include air temperature, barometric pressure and humidity in proximity to the respective animal.

The transceiver 26 is arranged to transmit and receive data stored on the module over the cellular network 18 to the central monitoring system. The The controller 28 includes a processor and a memory arranged to store sensed conditions from the condition sensors 24, position data determined by the position locator 22 as well as various criteria thereon. For each condition sensed by the condition sensors 24 the controller stores a prescribed condition criterion for comparison to the sensed condition to determine whether or not the health of the animal appears to be at risk. Various programming is also stored on the memory of the controller for executing the various functions of the system as described in further detail below.

The central monitoring system 16 is a server which may include one or more computers at one or more locations in the usual manner of a computer server. The central monitoring system 16 also includes a memory for storing data and programming thereon and a processor for executing the associated programming of the monitoring system to execute the various functions of the system 10 described below. The central monitoring system also includes a suitable communication element arranged to communicate by various means including over the internet, with a mobile network, a satellite network, a local wireless network or any combination thereof to both receive transmissions from the sensor modules 12 and to send corresponding communications to user devices, for example computers, mobile devices and the like, by various forms including SMS, e-mail, and the like.

When used for livestock, the system typically operates by configuring the sensor modules 12 to periodically sense the current position, a condition of the animal, and ambient conditions on an ongoing basis at a prescribed interval duration.

Each time the current position is checked it is compared against a previously determined position. If the position has substantially changed such that the distance between the current position and the previously determined position exceeds a prescribed threshold, then the current position is transmitted from the sensor module to the central monitoring system. If the position remains substantially unchanged, no transmission relating to position is necessary.

Alternatively, a change in position of the animal may be evaluated by providing additional conditions sensors on the module 12 which includes a gyro and/or accelerometer to determine acceleration and velocity/speed or sudden movements, a magnetometer to determine heading orientation movement, and barometer for elevation movements. These circuits are very low power consumption and can be used to determine at rest or in motion status by the central monitoring system instead of GPS circuits which can consume larger amounts of power and require longer times to get a fix such that the GPS circuits are generally only used to get accurate latitude, longitude and elevation once movement is detected with non GPS circuits.

Each time the conditions are periodically sensed by the condition sensors 24, the sensed conditions are compared to the relevant criteria stored on the controller, for example to determine if heart rate is too low or too high relative to respective thresholds or if the body temperature of the animal is too high or too low relative to respective thresholds. The sensed conditions are only transmitted if the sensed conditions are outside of the permissible range.

In each instance of a transmission from the sensor module to the central monitoring station, the transmission takes the form of a notification signal which includes the current position of the animal. If it is a sensed condition which is the basis for the notification signal, then the current sensed condition is also included with the current position in the notification signal transmitted to the central monitoring system.

At the central monitoring system, all sensed conditions including those of the animal and ambient conditions are recorded in memory for subsequent analysis. If a notification signal is received related to a sensed animal condition being outside of a permissible range, the central monitoring compares the sensed animal condition to previously sensed conditions of the animal to determine the amount of change in the condition. The central monitoring system also compares the change in animal condition to any corresponding change in ambient conditions over the same period. An alarm condition is only determined and a corresponding alert is sent from the central monitoring system to the owner of the animal if the change in animal condition cannot be explained by a corresponding change in ambient conditions. The alert can be sent to the mobile device of the user, a personal computer of the user, or the like, through any one of various communication means available to the central monitoring system.

Alternatively in the instance of the position of the animal changing being the basis of the notification signal, the central monitoring system performs a further comparison of the current position to boundary position data stored on the memory of the central monitoring system. The boundary position data relates to a geo fence representing a boundary 30 of an area where the animal is to be contained. If the current position is outside of the boundary data, then an alarm condition is determined and a corresponding alert including the position of the animal is sent to the owner of the animal by a signal transmitted to the mobile device of the user, a personal computer of the user, or the like through the various communication means available to the central monitoring system.

In either instance of an alarm condition being determined resulting from an out of bounds current position or a condition of the animal outside of the permissible range, the central monitoring system can transmit an instruction over the mobile network back to the corresponding sensor module to increase the frequency of the periodic measurements of condition and position of the animal, that is the interval duration between measurements is reduced.

The sensor module also stores an additional threshold thereon corresponding to the rate of change of the position of the animal indicative of the speed of movement of the animal across the ground. In this instance if the speed of the animal is determined to exceed the prescribed threshold as a result of the position over the interval duration changing too much, then the frequency of the determination of position is increased to have more frequent updates of the current position of the animal to the owner.

In an exemplary embodiment of the invention, the unit on the animal will transmit back at a predetermined time period, for example every 6 or 12 hours even if nothing has changed in sensed data so that the central monitoring system knows the battery didn't die or hardware failed on the animal. Hardware failure is an alarm condition to the owner or user.

In the event that the unit may also be removed from the animal, for example by a rustler, the removal can be detected as the sensed body temperature and vitals of the animal will change instantly. The owner can then be alerted quickly of theft in that manner as well.

In sending data, environmental conditions are also sent such as air temperature, barometric pressure, and humidity for each animal. The central monitoring systems use these conditions for determining animal health or predicting potential hazardous conditions for an animal which may even lead to loss of life of the animal. Much more can be done on the analytics and visualization of data (Big Data Paradym) either with a computer, laptop, tablet, smartphone, or other device. The detailed historical data on the animal is always available to the animal owner anytime, anywhere on any device they choose presented in an easy to read and see format, for example by providing an internet interface on the central monitoring system that users can log into.

In an alternative use for monitoring wild animal populations relative to roadways, the boundary position data stored on the central monitoring system corresponds to a geo fence at a prescribed threshold distance alongside roadways. A subscriber to the system 10 in this instance would download an application executable on their mobile device which subscribes them to the monitoring system. Using the position data available on the mobile device of the user, the executable application and/or the central monitoring system can determine when an animal crosses a boundary which is in sufficient proximity to the user to cause an alarm condition. If an alarm condition is determined an alert is sent to the user which indicates their proximity to a boundary which has been crossed by an animal or which may potentially be crossed by an animal due to their proximity to the boundary. Each subscriber of the system is only alerted of animals crossing boundaries in proximity to their current position. This system is particularly suited for warning persons driving on roadways of potential collisions with wild animals on the roadway.

Since various modifications can be made in my invention as herein above described, it is intended that all matter contained in the accompanying specification shall be interpreted as illustrative only and not in a limiting sense.

The invention claimed is:

1. A method of monitoring an animal comprising:
   i) providing a monitoring system including:
      a sensor module including a housing arranged to be carried on the animal, the housing of the sensor module including therein: a position locator arranged to receive position data from a satellite network and determine a current position of the animal, a transmitter, and a controller arranged to store a previously determined position of the animal thereon; and
      a central monitoring system located remotely from the animal which stores boundary position data representing a boundary thereon and which is arranged to communicate with the sensor module over a communications network;
   ii) sensing at intervals a position of the animal using the position locator of the sensor module;
   iii) at each interval comparing the current position to the previously determined position to determine a notification condition if the current position of the animal has substantially changed relative to the previously determined position using the controller of the sensor module;
iv) transmitting a notification signal which includes the current position to the central monitoring system over a network using the transmitter of the sensor module in response to determination of the notification condition;
v) upon receipt of the notification signal, comparing the current position to the boundary position data using the central monitoring system so as to determine an alarm condition if the current position is outside of the boundary represented by the boundary position data, but not determine an alarm condition until at least the next notification condition if the current position is within the boundary represented by the boundary position data; and
vi) sending an alert from the central monitoring system over the communications network if the alarm condition has been determined.

2. The method according to claim 1 including providing the current position with the alert.

3. The method according to claim 1 including increasing a frequency of the sensing at intervals of the position of the animal if an alarm condition has been determined.

4. The method according to claim 1 including increasing a frequency of the sensing at intervals of the position of the animal if a rate of change of the position exceeds a prescribed speed limit.

5. The method according to claim 1 wherein the communications network is a mobile phone communication network.

6. The method according to claim 1 including sending said alert from the central monitoring system to a plurality of subscribers if an alarm condition has been determined.

7. The method according to claim 6 wherein the boundary is defined alongside a roadway and the animal comprises a wild animal.

8. The method according to claim 1 including wherein the animal comprises a livestock animal.

9. The method according to claim 1 including providing a condition sensor on the sensor module which is arranged to sense a condition of the animal, storing a prescribed condition criterion on the controller of the sensor module, and transmitting a notification signal which includes the sensed condition of the animal to the central monitoring system if the sensed condition of the animal meets the prescribed condition criterion.

10. The method according to claim 9 wherein the condition of the animal is a heart rate of the animal or a body temperature of the animal.

11. The method according to claim 9 including comparing the sensed condition to a previously sensed condition and an ambient temperature to determine an alarm condition at the central monitoring system.

12. The method according to claim 11 including increasing a frequency of the sensing at intervals of the position of the animal if an alarm condition is determined.

13. The method according to claim 1 including supporting the housing of the sensor module on the animal using adhesive.

14. The method according to claim 1 including supporting the housing of the sensor module under a skin of the animal.

15. A method of monitoring an animal comprising:
i) providing a monitoring system including:
a sensor module including a housing arranged to be carried on the animal, a transmitter supported in the housing, a controller supported in the housing and arranged to store a prescribed condition criterion of the animal thereon the condition criterion comprising a permissible range, and a condition sensor in communication with the controller and which is arranged to be carried on the animal so as to sense a current condition of the animal; and
a central monitoring system located remotely from the animal which is arranged to communicate with the sensor module over a communications network and to store sensed conditions of the animal thereon;
ii) sensing at intervals a current condition of the animal using the condition sensor of the sensor module;
iii) at each interval comparing the current condition to the prescribed condition criterion to determine a notification condition using the controller of the sensor module if the current condition of the animal is outside of the permissible range of the prescribed condition criterion; and
iv) at each interval transmitting a notification signal which includes the current condition of the animal to the central monitoring system and storing the current condition of the animal on the central monitoring system only if the notification condition has been met; and
v) upon receipt of a notification signal, using the central monitoring system to i) compare the current condition to at least one of the conditions of the animal that was previously sensed by the condition sensor and stored on the central monitoring station and ii) determine an alarm condition based at least in part on an amount of change in the current condition relative to the said at least one of the conditions of the animal that was previously sensed by the condition sensor; and
vi) sending an alert from the central monitoring system over the communications network if an alarm condition has been determined.

16. The method according to claim 15 wherein the condition of the animal is a heart rate of the animal or a body temperature of the animal.

17. The method according to claim 15 including comparing the current condition to an ambient temperature in addition to said at least one of the previously sensed conditions of the animal to determine the alarm condition at the central monitoring system.

18. The method according to claim 17 including increasing a frequency of the sensing at intervals of the current condition of the animal if the alarm condition is determined.

19. The method according to claim 15 including transmitting a current position of the animal with the notification signal.

20. The method according to claim 1 wherein the sensor module includes a movement sensor including an accelerometer component, and wherein the method includes determining if a change in position of the animal has occurred using the accelerometer of the movement sensor and sensing the position of the animal using the position locator of the sensor module only subsequent to determination that the change in position of the animal has occurred using the accelerometer of the movement sensor.

* * * * *